(12) United States Patent
Tveitevoll et al.

(10) Patent No.: US 12,263,380 B2
(45) Date of Patent: Apr. 1, 2025

(54) METHOD FOR CONTINUOUS MEASUREMENT OF AND REGULATORY FEEDBACK FOR STRENGTH-TRAINING (71) Applicant: Alphatek AS, Randaberg (NO)

(72) Inventors: Åsmund Tveitevoll, Stavanger (NO); Olav Risa, Randaberg (NO); Erik Vassøy Olsen, Sola (NO); Aleksander Kristiansen Ferkingstad, Stavanger (NO); Ola Næss Kaldestad, Ulset (NO)

(73) Assignee: Alphatek AS, Randaberg (NO)

( * ) Notice: Subject to any disclaimer, the term of this patent is extended or adjusted under 35 U.S.C. 154(b) by 128 days.

(21) Appl. No.: 18/266,211

(22) PCT Filed: Dec. 9, 2021

(86) PCT No.: PCT/NO2021/050258
§ 371 (c)(1),
(2) Date: Jun. 8, 2023

(87) PCT Pub. No.: WO2022/124911
PCT Pub. Date: Jun. 16, 2022

(65) Prior Publication Data
US 2024/0033577 A1    Feb. 1, 2024

(30) Foreign Application Priority Data
Dec. 10, 2020 (NO) .................................. 20201357

(51) Int. Cl.
*A63B 24/00* (2006.01)
*A63B 23/04* (2006.01)
*A63B 71/06* (2006.01)

(52) U.S. Cl.
CPC ...... *A63B 24/0075* (2013.01); *A63B 23/0405* (2013.01); *A63B 71/0622* (2013.01);
(Continued)

(58) Field of Classification Search
CPC ............ A63B 24/0075; A63B 23/0405; A63B 71/0622; A63B 2023/0411;
(Continued)

(56) References Cited

U.S. PATENT DOCUMENTS 9,011,301 B2 * 4/2015 Balandis .............. A63B 21/169
     482/114
9,814,920 B1 * 11/2017 Monterrey ......... A63B 21/0552
(Continued)

FOREIGN PATENT DOCUMENTS

KR        101648044 B1    8/2016
KR        102031243 B1   10/2019
(Continued)

OTHER PUBLICATIONS

Patentstyret Norwegian Industrial Property Office, Search Report for Norwegian Patent Application No. 20201357 dated Jul. 10, 2021, 2 pages.
(Continued)

*Primary Examiner* — Sundhara M Ganesan
(74) *Attorney, Agent, or Firm* — Bradley Arant Boult Cummings LLP (57) ABSTRACT

It is described a method for continuous measurement of, and regulatory feedback for, strength-training where the reaction forces from a person with a lifting weight that is standing on a surface, is transferred through the surface, said method comprising the following steps: a. measure a force in vertical direction (Z-direction) on one or more plates attached to one or more load cells; b. use the force measurement in step a) to continuous calculating the velocity of, and relative movement of the combined center of mass of the person and the lifting weight, c. provide feedback in real-time to the user, where the feedback relates to velocity and/or lifting distance
(Continued)

in relation to predefined values and/or generated values, in order to the user to adjust the training based on the feedback.

9 Claims, 5 Drawing Sheets

(52) U.S. Cl.
CPC ............ *A63B 2023/0411* (2013.01); *A63B 2024/0068* (2013.01); *A63B 2071/0625* (2013.01); *A63B 2071/0647* (2013.01); *A63B 2071/0655* (2013.01); *A63B 2071/0675* (2013.01); *A63B 2208/0204* (2013.01); *A63B 2214/00* (2020.08); *A63B 2220/36* (2013.01); *A63B 2220/52* (2013.01); *A63B 2220/58* (2013.01)

(58) Field of Classification Search
CPC .... A63B 2024/0068; A63B 2071/0625; A63B 2071/0647; A63B 2071/0655; A63B 2071/0675; A63B 2208/0204; A63B 2214/00; A63B 2220/36; A63B 2220/52; A63B 2220/58; A63B 2244/09; A63B 2071/065; A63B 21/0724; A63B 23/03516; A63B 23/03525; A63B 23/00; A63B 24/00; A61B 5/1036; A61B 5/11; A61B 5/1116; A61B 5/224; G09B 19/0038

See application file for complete search history.

(56) References Cited

U.S. PATENT DOCUMENTS

| | | | |
|---|---|---|---|
| 2014/0073492 A1* | 3/2014 | Hunter | A63B 21/0615 482/98 |
| 2019/0344115 A1 | 11/2019 | Neuhaus et al. | |
| 2020/0368581 A1 | 11/2020 | Cobb et al. | |
| 2021/0016150 A1* | 1/2021 | Jeong | A61B 5/1036 |
| 2023/0078368 A1* | 3/2023 | Deland | A63B 24/0062 482/8 |

FOREIGN PATENT DOCUMENTS

| | | |
|---|---|---|
| RU | 2658255 C1 | 6/2018 |
| WO | WO-2015048884 A1 | 4/2015 |
| WO | WO-2020019041 A1 | 1/2020 |

OTHER PUBLICATIONS

Patent Cooperation Treaty, International Search Report for International Application No. PCT/NO2021/050258 dated Feb. 18, 2022, 3 pages.

* cited by examiner

METHOD FOR CONTINUOUS MEASUREMENT OF AND REGULATORY FEEDBACK FOR STRENGTH-TRAINING

TECHNICAL FIELD

The present invention relates to a method for continuous measurement of and regulating feedback for strength-training, where the reaction forces from a person with a lifting weight that is standing on a surface, is transferred through the surface. More specifically, the invention relates to a method for measuring the velocity of the center of mass when training with free weights and using these data to provide the user with regulatory feedback in real time.

BACKGROUND ART

Cardiovascular training has for many years had good valid and reliable measurement for the intensity and degree of fatigue (oxygen intake, lactate measurements, velocity and pulse measurements) during endurance exercises, and especially running speed and heart rate have been available for users with GPS watches with heart rate monitor. Within the field of weight-lifting, this type of technological aids to measure the key variables have not been available.

Strength-training is a workout type which are used to strengthen and develop different physiological systems of the body, among others the muscle-skeletal system. The result of the strength-training is dependent on how the different variables are weighted, for example intensity/relative load, degree of fatigue, effort, concentric and eccentric lifting speed, range of motion (ROM) etc. By load is meant the number of kilos lifted by the athlete. Intensity and degree of exhaustion seems to be very important to achieve the desired result of the training.

Intensity has traditionally been measured by % of 1 RM (1 repetition maximum) which is an expression for the maximal load one can lift with only one repetition in a certain exercise. 1 RM or XRM (the specific load which can be performed X times in a series to exhaustion), degree of fatigue has been measured subjectively with a RPE-scale (scale that range from 1-10 that rates the effort for the user during a lifting set).

The drawback of using a fixed value of 1 RM as chosen load/intensity is that the daily form can be influenced by a number of different factors such as sleep quality, diet, caffein, stress, emotions etc. Hence the actual daily 1 RM can vary as much as 20% from workout to workout. The result of this is can be that something that should be very easy becomes very heavy. This can affect both the result and increase the risk of injury.

This problem can be solved by monitoring the lifting velocity at the different relative loads, since the lifting velocity will decrease as the load increases. A reliable measurement method will then be to lift with maximum lifting velocity at a certain load (preferably between 40-60% of 1 RM) and thereby measuring the physical form of the user within a given time frame. This can be used to estimate 1 RM which can be used to choose the best load for the given workout and hence increase the results and reduce the risk of injury.

A set of resistance training performed until exhaustion with maximum lifting velocity, will have a declining concentric lifting velocity. Concentric lifting velocity is when the muscles contract to develop force. Monitoring the lifting velocity and decrease of lifting velocity will give an objective measurement of the degree of fatigue. Decrease of lifting velocity demonstrates a strong correlation with restitution time, the progress in strength and muscle growth the user has. Workouts where the user is close to exhaustion and with a large decrease in lifting velocity gives a long restitution time without any improvements in strength and muscle growth.

Visually or auditive feedback regarding technique and lifting velocity through objective measurements or assessment of a coach will give better results than exercising without any feedback. Having a coach present to provide feed-back, will be resource-demanding. There will also be several variables that even a trained eye cannot see and hence valuable feed-back can get lost.

Autoregulation is used to modify the load on the strength training based on the daily form. The methods that are used today are primitive and are mostly about limiting the number of repetitions or number of workout sets based on experienced effort. The idea is that the workout load should be lower if the restitution is insufficient. These kinds of workout sets will minimize the risk of injury, which will make the user stronger in the long run.

Velocity based training is the best method for autoregulating workouts. Today, there are three main groups of sensors which can be used for measuring the squatting velocity with a barbell. These are accelerometer (attached to the barbell), linear encoders (attached to the barbell) or photo/video systems (markers attached to the barbell). The velocity is monitored for each lift and as the user is getting tired, the velocity will fall outside a defined velocity range. The lifting velocity for a given load can also tell the users how good their daily form is, expressed as estimated 1 RM, and thereby decide whether the user should train with a large or small training volume, high or low relative load or degree of fatigue.

RU 2658255C1 describes a device which registers the movement of the mass center of a barbell, based of markers attached to both ends of the barbell. A dynamometer platform is directly built into the weightlifting platform.

From WO 2020019041 it is known a device for deciding one or more movement-related parameters for a barbell, which includes a sleeve provided around the barbell. The sleeve comprises a plurality of distance sensors which are concentrically provided around the sleeve. Each distance sensor is capable of measuring a distance between the sleeve and an opposite surface. A processor can process all the data from a given sensor and decide the movement of the barbell over time.

KR 10203124381 teaches an apparatus for measuring movement during weight-lifting where the apparatus comprises a camera to measure the user's physical dimensions and a sensor unit which a.o. can be a pressure sensor plate.

WO 2015048884 A1 describes a user sensor device which is carried by the user during exercise. The sensor device measures acceleration, orientation and other information from the user during workout. The workout may be weight-lifting. The sensor device transmits the recorded data to a mobile device for processing and the mobile device can display the interpreted data in a graphical interface. The user may use this information to plan the workout and measure the progression of the workout.

The existing solutions have several drawbacks:
- every user must bring his own personal equipment to the exercise;
- they measure the barbell velocity and does not include the body's own mass into account in the movement. Consequently, the performed measurement is therefore an indirect measure.

the barbell velocity is heavy affected by anthropometric measures (mass and mass distribution of the person, length of limbs), weight distribution and technique in addition to length of the femur, which may influence the techniques in squats. Estimated 1 RM by this methods does not seem to correlate with the actual 1 RM, and small technical changes can make a big difference. The fact that all individuals have different anthropometric measures makes the general recommendations regarding relative load based on barbell velocity does not seem usable for individual calculations.

prior to the lift, the user must input the load of the barbell. Wrongly calibrated weight plates or erroneous input can lead to faulty measurements which will give faulty autoregulation of the exercise load and degree of fatigue.

encoders and accelerometers are fragile equipment which can easily be damaged.

photo/video-measurements require skilled professionals and equipment which are only suitable for laboratory use.

the prior art are using technologies that makes it difficult to give direct feedback regarding the workout without help from others.

SUMMARY OF INVENTION

In other to solve the above mentioned problems and challenges, present invention provides a method for continuous measurement of and regulatory feedback for strength training, where the reaction forces from a person with a barbell standing on a surface, is going through the surface, said surface comprises one or more plate attached to one or more load cells, said method is characterized by the following steps:

a. measure a force in the vertical direction (Z-direction) on one or more plates attached to one or more loadcells, b. use the force measurement of step a) to continuously calculate the velocity and relative movement of the combined center of mass of the person and the lifted weights in the vertical direction (Z-direction), c. provide the user with real time feedback, where the feedback relates to velocity and/or lifting distance in relation to predefined values and/or generated values, in order for the user to regulate the training based on the feedback.

If the user is supposed to work on strength and shall have a certain lifting velocity, the system will give feedback to the user that the velocity is too high.

Step c) may include providing real-time feedback via one or more of a screen, sound, light and haptics.

According to a preferred embodiment, the method comprises a step of obtaining the user's weight and weight lifted with a weighing-in procedure, comprising:

i) weighing the user without a lifting weight;
ii) weighing the user with the lifting weight; and
iii) calculating the lifting weight's mass based on the weighing in step i) and step ii).

Further, the method according to the invention comprises:

d) saving the user-specific measurement data, where the measurement data is stored on the user's profile after login.

According to a preferred embodiment, the user selects the training mode using a menu system, where the user navigates the menu by using the plate. The loadcells record force and will register the user's movements on the plate.

Preferably, the method according to the inventions comprises generating personal parameters for regulatory feedback based on the historical data of one or more users.

Preferably, the calculations are performed on a plate, server or on front-end.

Furthermore, the method comprises calculating the user's relative position in the horizontal plane based on the difference of the load cells over time.

In a preferred embodiment, the method comprises comparing the velocity of the mass center with one or more predefined variables based on velocity profiles related to specific muscle qualities, and further comprises giving the user feedback regarding the velocity in relation to a predefined zone.

The measured data is the reaction force from the user on the plate. This is measured with a sufficiently high sampling rate, based on the exercise that is being performed. The changes in the reaction force is used to calculate the velocity of the center of mass with a model based on empirical data. In contract to the barbell velocity, the velocity of the center of mass will be more comparable for users with different weight and body shape. This makes it possible to generate general velocity profiles which can be used for to train specific exercise qualities and autoregulate the workout by telling the user to increase the load when the velocity is too high and stop before the loss of velocity becomes too large.

DETAILED DESCRIPTION OF THE INVENTION

The force platform (102) comprises a flat, stiff plate connected to one or more, for example four, load cells (105) that can measure acceleration from a user's movements when standing on the plate (102). Typical sampling rate is often between 400 Hz and 1000 Hz. The combination of data from force and time, can be used to calculate a number of parameters which are relevant for the workout. These parameters comprises:

maximum force,
the velocity of the center of mass,
relative movement of the center of mass in z-direction (vertical direction) (see FIG. 2),
work
power
balance. If more than on load cell is used, the balance can be measured looking at the difference between the load cells.

Figure 1:
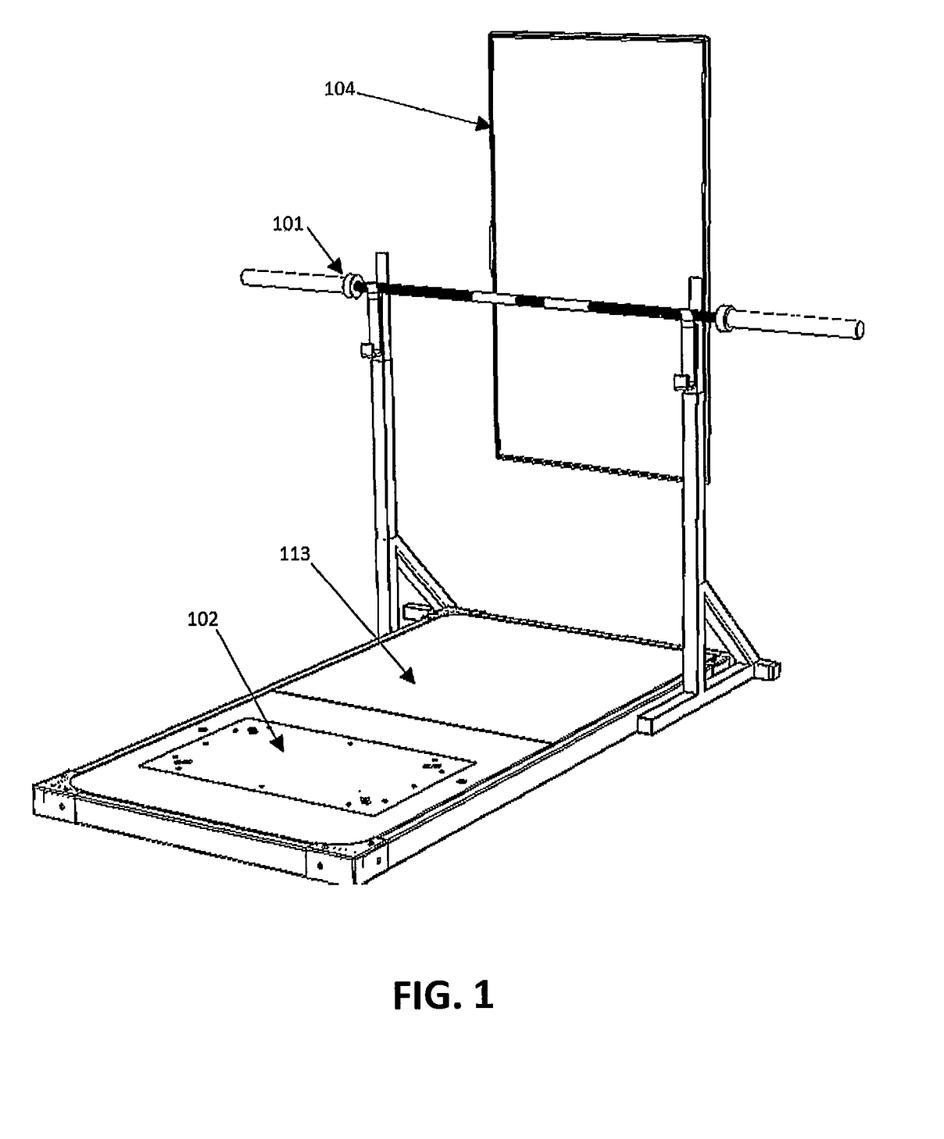
FIG. 1 shows an embodiment of a device for use in the method according to the invention.
Figure 2:
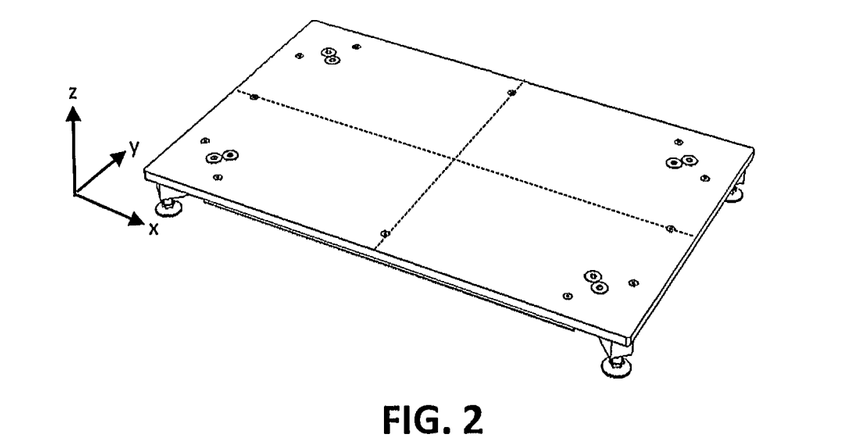
FIG. 2 shows the coordinate system related to the force platform.
Figure 3:
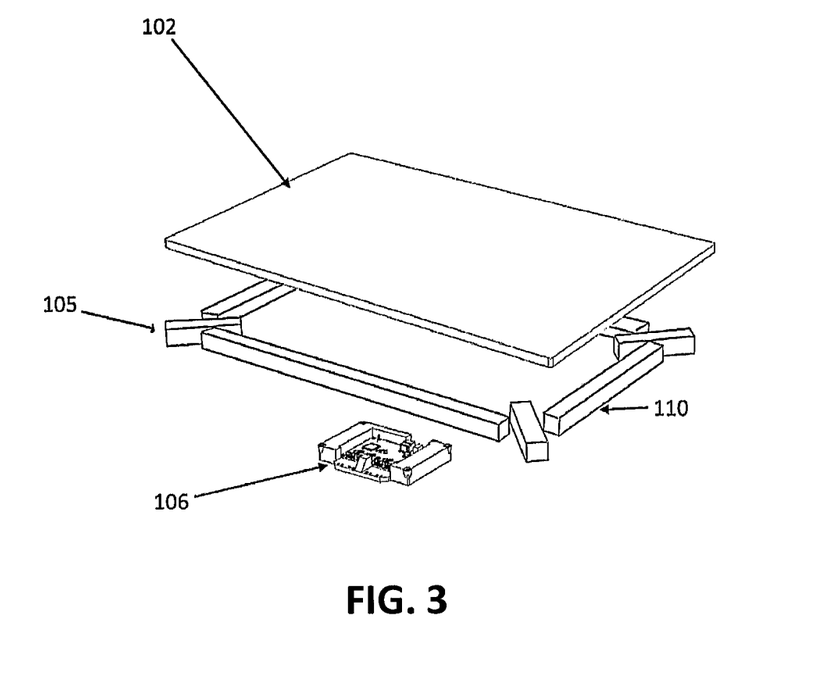
FIG. 3 shows one embodiment of the force platform.

The force platform (102) can for example be lowered into a floor (103) locking all the degrees of freedom except for movement in positive z-direction (see FIG. 1 and FIG. 2). A display is provided directly in front of the user (104) which is oriented such that the short sides of the display are parallel with the floor. A squatting rack (101) can be positioned between the force platform and the tv-screen. It can be possible to operate the device without assistance from others.

Figure 5:
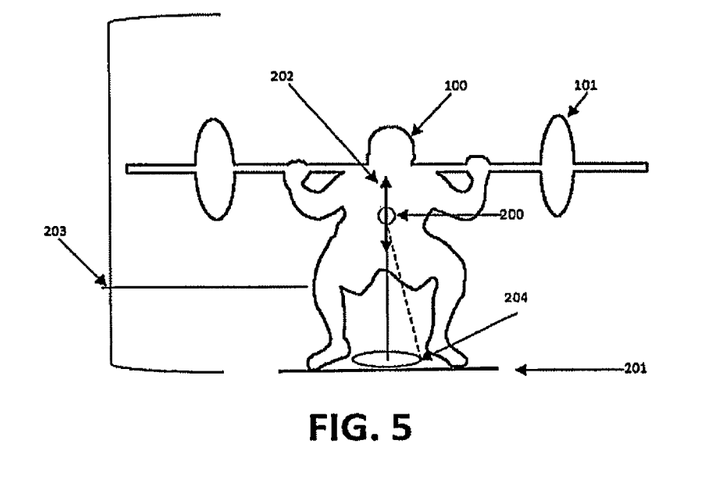
FIG. 5 shows recorded parameters.

The data processing unit (106) comprises several inputs that are independent of each other and can therefore measure several load cells (105) simultaneously. By measuring the total weight on each of the plate's long sides, it is possible to find the position of the center of mass in the y-direction (coordinate system described in FIG. 2). The same applies for the total weight for each of the short sides for the x-direction. With external input, for example if a person is standing og the plate, the user's center of mass (204) can be detected by this method (see FIG. 5).

Figure 7:
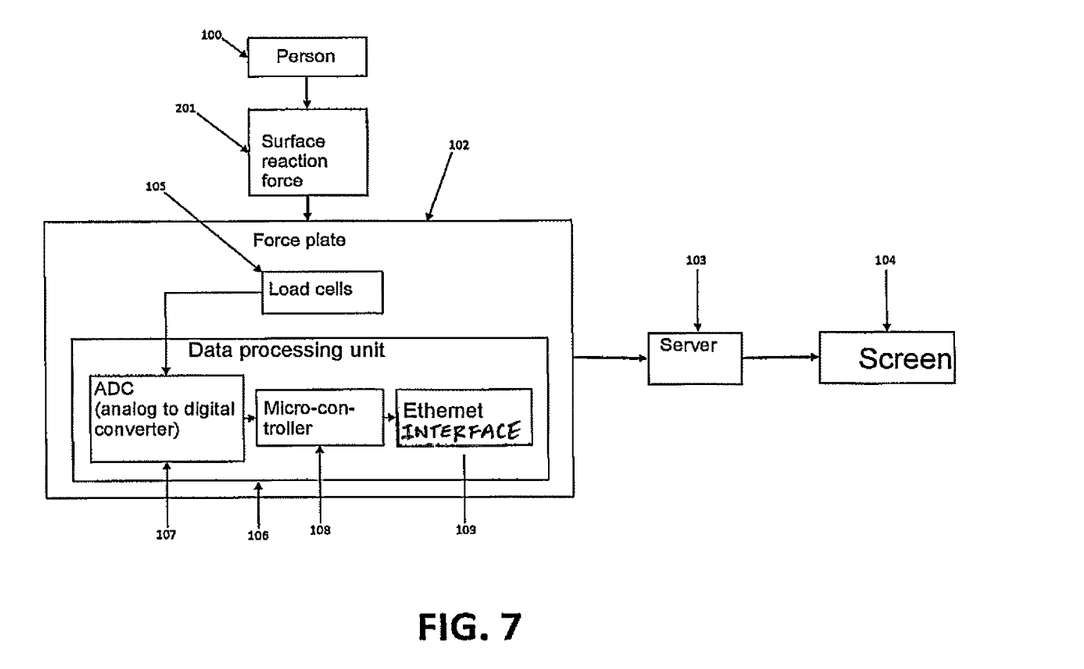
FIG. 7 is a block diagram showing the elements of a device that can be uses to perform the method according to the invention.

The data processing unit (106) reads the load cells (105) by analogue-to-digital converters (107). Each of the independent inputs has an individual analogue-to-digital (A/D) converter driven by a common high precision clock pulse and thus simultaneous readings of the connected load cells (105) are obtained. The connection of the loadcells to the A/D converter ensures a ratiometric measurement because the operating voltage of the loadcell is the same as the reference to the A/D converters. The readings can be done by looking at the voltage difference over the loadcell. The recorded measurement data is transmitted by a digital protocol to a micro controller (108). The readings are transmitted further from the microcontroller to the network server (103) through an interface (109), see FIG. 7. The interface can for example be Wi-Fi, Bluetooth, Canbus or RS232.

The calculated center of mass (204) can be illustrated as a point on the screen (404). The center of mass is handled as coordinates in the x- and y-plane for the power board's x- and y-axis respectively. These coordinates are further transformed with respect to the desired sensitivity and the resolution of the display. The transformed coordinates are being visualized on the display as a point. The user can control this mass center by changing where the mass center is on the board. The user can then lean forward/backwards and/or to the right or the left. This method is used to navigate a menu system to choose mode and exercise (FIG. 10). The user will then have possibility to choose different modes on the board such as: standard exercise (400), velocity controlled exercise (401), testing (402) or game (403). To choose a given mode, the user will have to move the mass center on the board, such that the point (404) coincides with one of the boxes illustrated in FIG. 10. The system will then automatically adjust the measuring frequency and choose the algorithms used to interpret the raw data.

In velocity-based training mode, the user will choose a given velocity profile before the workout starts. Velocity profile in this respect, means a velocity linked to a specific muscle quality such as for example speed or strength. The screen will be able to give a feedback to the user if the velocity is within the actual velocity profile for example by use of a traffic light function. At green light, the user is well within the velocity profile, at yellow light, the user is prone to fall out of the velocity profile and at red light, the exercise should halt because the lifting velocity is outside the given velocity profile.

With different objectives for the strength training, for optimal progress of a series of repetitions with maximum lifting speed, the user should use a load that is giving a certain velocity. Workouts performed for increasing the neuromuscular maximum force development, should for example be performed with a load that gives a mean propulsive velocity of 0.3 to 0.5 m/s, i.e. the average velocity as long as the acceleration is positive.

Under a series of repetitions performed with maximum lifting velocity, the effect of the workout on the ability for maximum strength development will be increasing up to about 15-20% loss in lifting velocity. Thereafter, the total effect of the workout will be less. To interrupt a series at the correct time will is crucial for how effective the workout is to achieve the desired muscle quality.

The system is capable of measuring the velocity of the center of mass (202), something that differentiate it from prior art. With the methods that are existing today, it is only possible to measure the velocity of a barbell (101), but this is an indirect measure that does not take the body shape and the weight of the user into account. The weight that is being lifted needs to be manually given to the system. Because of this, all users must have individual velocity zones for specific muscle qualities. This can be found by testing. In this respect, with muscle qualities is meant strength, muscle growth, force and velocity. This will make it possible to make general velocity profiles which that ca be valid for users with different weight and body form.

Data processing and algorithm calculations can be done on the data processing unit (106), the network server (103) or in front end of a screen (104). General data flow is depicted in FIG. 9. The information from the force platform (105) is streamed directly to a real-time server for further processing. Subsequently, the data is sent to the real-time screen (104) and storage server (111). The real-time screen will give the user feedback during the workout which makes the user able to take critical decisions based on the feedback on the screen. Data sent to the storage server is meant as a tool to analyze historical data and progression. These data can be illustrated in for example a web-app (112) on the user's personal computer or mobile phone. These data will be stored on each user's respective user profile by a unique identifier. All date that is stored after this identifier is activated will be stored to the user. User data will also be user to further develop the algorithms and regulatory feedback.

The system makes continuous measurements, this means that both direct and indirect measurements (e.g. power, velocity, distance and work) are kept updated when the system is in use. This can be done either for every new data package from the sensors or for a defined or variable number of data packages. The system will in other words have information about the data load at any point during use.

Feedback to the user is provided in real time, which means that feedback from the system is given to the user in the moment it is available relevant. Hence, the user shall not have to wait until after a set to get information about single lifts, and he does not have to wait until the end of the workout to receive information regarding individual sets.

Neither for regulatory the user should not have to wait for a finished set or workout, but instead receive immediately when they are available and relevant. Regulatory feedback means that the user is given a message regarding changes the user will have to perform himself, for example change weights, stop lifting, or make changes to his lifting technique. For example the user want to receive regulatory feedback for weight based on lifting velocity, and receive relevant feedback immediately after the "continuous measurements" require that the user should adjust the weight.

Figure 4:
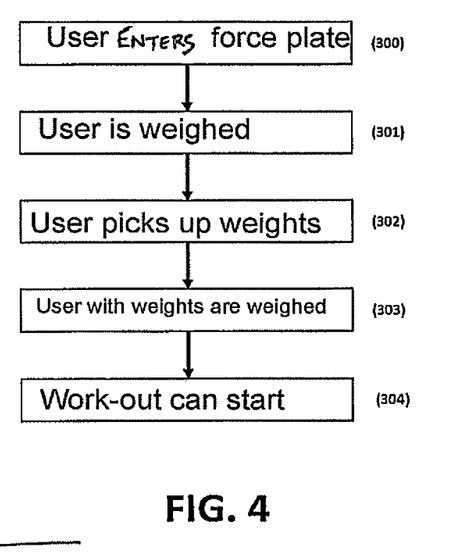
FIG. 4 is a schematical representation of a weigh-in procedure.

If the weight lifted by the user should be stored, the weight which is lifted can for example be automatically registered in that the user is being guided through a weigh-in procedure (FIG. 4). The user is firstly weighed in without a weight and thereafter with a weight, and the real-time server will automatically calculate the weight difference and use this further in other relevant calculations without the user have to provide any further input to the system.

By measuring changes of acceleration when the user lifts weights on the plate, it will be possible to calculate the relative movement and velocity of the center of mass in the vertical direction (z-direction). In step 4 of the weigh-in procedure, the total weight of the user and weight is found (see FIG. 4, 303). The system sets this weight as a zero point and assume that the mass is conserved throughout the workout. The velocity of the center of mass can then be found by integrating the acceleration with regards to time.

Figure 6:
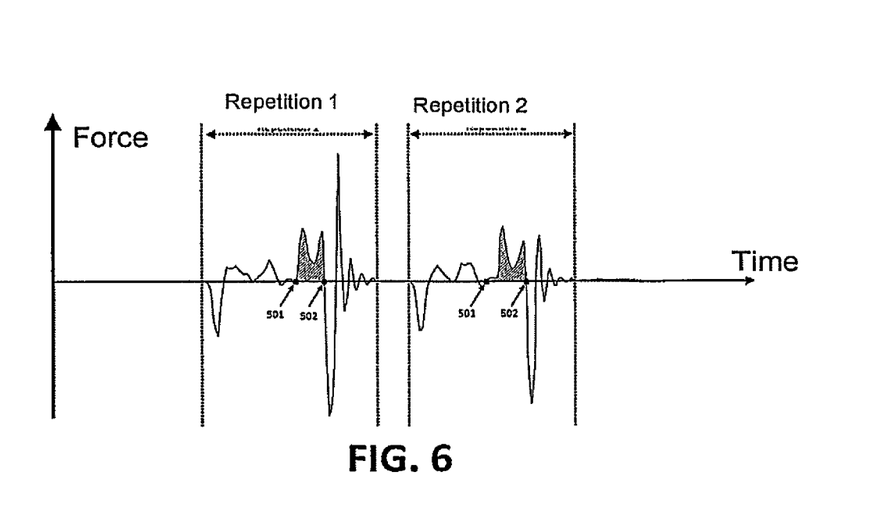
FIG. 6 shows an example of a graph from a squatting session.

The mean velocity at positive acceleration in concentric phase is calculated by integrating the acceleration in the area between 501 and 502 in FIG. 6, where the integral only is valid if the acceleration is positive. Maximum velocity in concentric phase us calculated by integrating acceleration with regards to time in the area between 501 and 506 in FIG. 6.

The pressure center (204) is defined as the user's center of mass reflected in the X,Y-plane (FIG. 2). Displacement of the pressure center is calculated by summing up the load on the lead cells (105) both on the short side and long side of the plate in real time. The resultant force is thereafter calculated both in x and y direction by looking at the difference between the two short sides and the two long sides.

Figure 8:
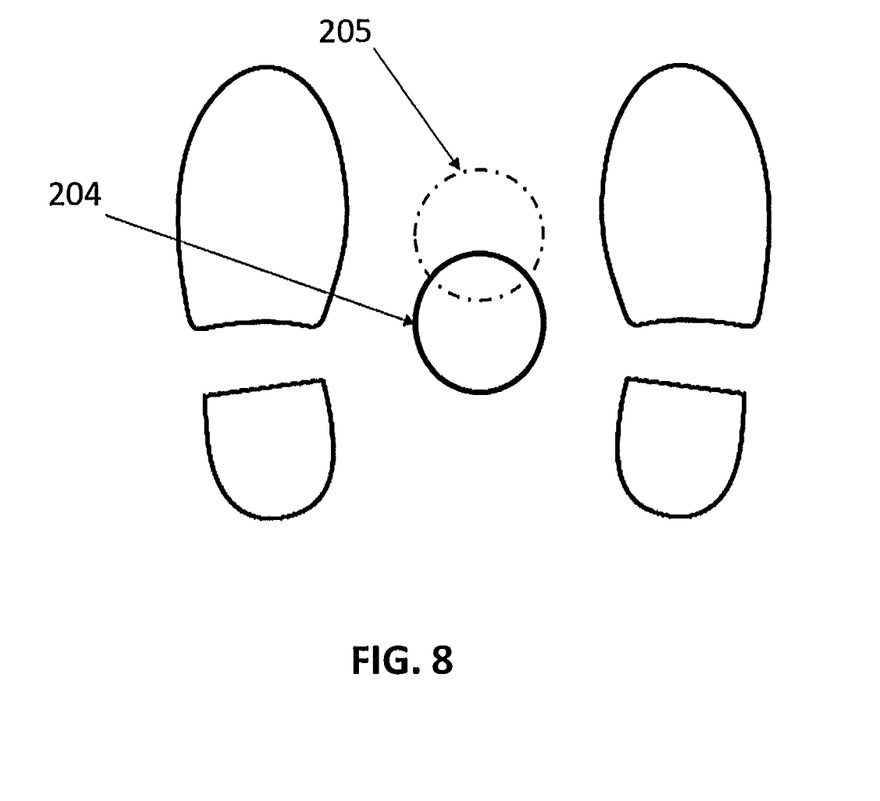
FIG. 8 is graphical representation showing the center of pressure.

The relative pressure center (204) is set in relation to the geometrical center on the plate during step 4 (303) during the weigh-in procedure. During lifting, a comparison is made of the relationship between the relative pressure center (204) and measured pressure center (205), see FIG. 8. This is used for estimating the stability of the lift and to reveal instability and unwanted movement pattern such as keeping the pressure on the heel during the complete lift.

The maximum reaction force in the concentric phase (the area between 501 and 502) is a measure which can tell something about the explosivity of the actual user on the plate.

Effect is defined as the reaction force multiplied by the velocity in the concentric phase (area between 501 and 502). Mean effect is force measured by the plate/man velocity between these points, while the maximum effect is the highest effect obtained by the user between these points with a given measurement frequency i.e. power measured by the plate/maximum velocity. This tells something about how much force the user is able to make use of at a given load with maximum effort.

1 RM is being estimated by performing the lift with a sub-maximum load with maximum concentric lifting velocity. The system is measuring the mean movement velocity of the center of mass in the propulsive concentric phase of the lift. This value corresponds to a relative share of 1 RM and can therefore be used to estimate this.

Hence the estimation of 1 RM can be done during warm-up, where the user lifts a weight which is considerably lighter than the actual 1 RM weight. This will make it possible to adjust the workout after 1 RM on each workout based on the form of the day. Consequently, this will reduce both the time of restitution and the risk of injuries.

When the 1 RM function is used, the user will receive proposals on the screen (104) regarding which load is recommended after warm-up.

Regulatory feedback in connection with training, is usually performed by use of constant parameters which are supposed to be valid for different persons. By using a system which can regulate these parameters on an individual level and by storing the individual's progression over time, it is possible to find a correlation between these parameters and the individual's progression over time. These data can then be used to:
 a) improve the limit values for lifting velocity and distance which will be suitable for the user,
 b) develop models guiding the regulatory feedbacks as a function of present form,
 c) develop constants and/or models in an individual and/or general level.

Two develop this, it is required potentially huge amounts of data, but also much labor with the present equipment, since the collection of data and the analysis is fully or partly manually. The present system makes it possible to collect these data during normal exercise, something which simplifies the data collection process, and also makes it possible to actively develop and improve the constants and/or models over time by use of technologies such a machine learning.

It will be obvious for a skilled person in the art that the method according to the invention also can be used for other strength-exercises, where the user exerts indirect or direct pressure on a foundation or a measuring device.

The invention claimed is:

1. A method for continuous measurement of and regulatory feedback for strength-training where the reaction forces from a person with a lifting weight that is standing on a surface, is transferred through the surface, the surface comprises one or more plates attached to one or more load cells, the method comprising:
 a. measuring a force in vertical direction (Z-direction) on the one or more plates attached to one or more load cells;
 b. using the force measurement in step a) to continuously calculate the velocity and relative movement of the combined center of mass of the person and the lifting weight in the vertical direction (Z-direction),
 c. providing feedback in real-time to the user, where the feedback relates to at least one of velocity and lifting distance in relation to at least one of predefined values and generated values, in order to the user to adjust the training based on the feedback.

2. The method according to claim 1, where step c) comprises giving feedback in real time by one or more of a screen, sound, light, and haptics.

3. The method according to claim 1, comprising:
 i. weighing the user without a lifting weight;
 ii. weighing the user with the lifting weight; and
 iii. calculating the weight of the lifting weight based on the weighing in step i) and step ii).

4. The method according to claim 2, further comprising:
 d) storing user-specific measurement data; and
 wherein the measurement data is stored on the user's profile after log-in.

5. The method according to claim 1, wherein:
 the user selects the training mode using a menu system; and
 the user navigates the menu by using the plate.

6. The method according to claim 1, comprising generating personal parameters for regulatory feedback based on historical data of one or more users.

7. The method according to claim 1, wherein the calculations are performed on a plate, server or front-end.

8. The method according to claim 1, further comprising calculating the relative position of the user in the horizontal plane based on the difference between the load cells over time.

9. The method according to claim 1, further comprising comparing the velocity of the mass center with one or more predefined variables based on velocity zones related to specific muscle qualities and further comprising giving the user feedback regarding the velocity in relation to a predefined zone.

* * * * *